(12) United States Patent
Izuhara et al.

(10) Patent No.: US 7,831,291 B2
(45) Date of Patent: Nov. 9, 2010

(54) SUBJECT MOVING APPARATUS AND IMAGING APPARATUS

(75) Inventors: Akira Izuhara, Tokyo (JP); Katsumi Azu, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1491 days.

(21) Appl. No.: 11/200,812

(22) Filed: Aug. 10, 2005

(65) Prior Publication Data

US 2006/0058639 A1    Mar. 16, 2006

(30) Foreign Application Priority Data

Aug. 27, 2004    (JP) .............................. 2004-248289

(51) Int. Cl.
A47B 71/00    (2006.01)
A61B 5/05    (2006.01)

(52) U.S. Cl. .................. 600/415; 600/407; 600/425; 5/600

(58) Field of Classification Search .............. 600/413, 600/407, 601, 658–663, 425, 415; 5/601, 5/425, 658, 427, 428, 430; 340/539.11; 378/205, 378/196, 4, 209
See application file for complete search history.

(56) References Cited

U.S. PATENT DOCUMENTS

| | | | |
|---|---|---|---|
| 4,583,242 A | 4/1986 | Vinegar et al. | |
| 5,525,905 A | 6/1996 | Mohapatra et al. | |
| 5,638,419 A | 6/1997 | Ingwersen | |
| 5,960,054 A | 9/1999 | Freeman et al. | |
| 6,094,760 A * | 8/2000 | Nonaka et al. | 5/601 |
| 6,460,206 B1 * | 10/2002 | Blasche et al. | 5/601 |
| 6,493,571 B1 | 12/2002 | Bis et al. | |
| 6,561,695 B2 | 5/2003 | Proksa | |
| 7,500,280 B2 * | 3/2009 | Dixon et al. | 5/713 |
| 2001/0025142 A1 | 9/2001 | Wessels et al. | |
| 2002/0120986 A1 * | 9/2002 | Erbel et al. | 5/601 |
| 2004/0199072 A1 | 10/2004 | Sprouse et al. | |
| 2005/0008116 A1 | 1/2005 | Nishide et al. | |

FOREIGN PATENT DOCUMENTS

| | | |
|---|---|---|
| DE | 2229220 A1 | 1/1974 |
| DE | 69912175 T2 | 7/2004 |
| EP | 0744158 A2 | 11/1996 |
| JP | 6211434 | 1/1987 |
| JP | 03012127 | 1/1991 |
| JP | 06014913 | 1/1994 |

(Continued)

OTHER PUBLICATIONS

Partial English translation for Japanese Reference No. 62-11434, p. 2 upper left, line 1-19.

(Continued)

*Primary Examiner*—Eric F Winakur
*Assistant Examiner*—Lawrence N Laryea
(74) *Attorney, Agent, or Firm*—Armstrong Teasdale LLP

(57) ABSTRACT

A cradle position sensing mechanism that includes a scale unit having a scale, which is used to detect the position of the cradle, formed thereon and being extended to cover a sliding range within which the cradle can be slid; and a sensor unit that moves in the directions, in which the scale unit is extended, along with the slide of the cradle so as to detect the scale of the scale unit. The cradle position sensing mechanism serves as a digital linear encoder. Based on the reading on the scale detected by the sensor, the cradle position sensing mechanism calculates the position into which the cradle is slid.

16 Claims, 6 Drawing Sheets

FOREIGN PATENT DOCUMENTS

| | | |
|---|---|---|
| JP | 10-314162 | 12/1998 |
| JP | 2002165780 | 6/2002 |

OTHER PUBLICATIONS

Muthuvelan Varadharajulu; "Table Control Method and Table System"; U.S. Appl. No. 10/704,837, filed Nov. 10, 2003; 15 pgs.

Akira Izuhara; "Parallel-Link Table and Tomographic Imaging Apparatus"; U.S. Appl. No. 10/719,074, filed Nov. 21, 2003; 25 pgs.

Muthuvelan Varadharajulu; Table Control Mehtod, Patient Supporting Device, and X-Ray Imaging Apparatus; U.S. Appl. No. 10/964,309, filed Oct. 12, 2004; 11 pgs.

* cited by examiner

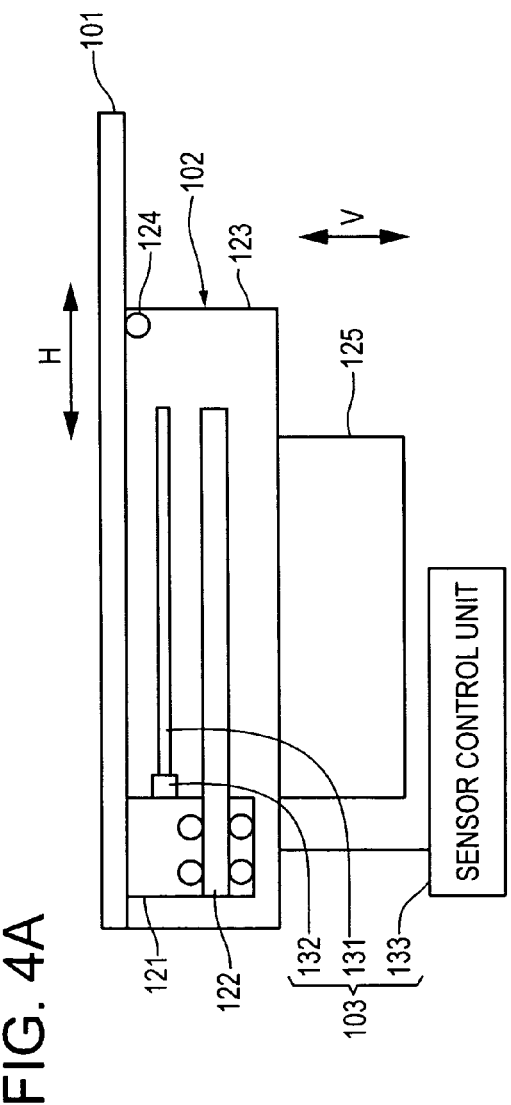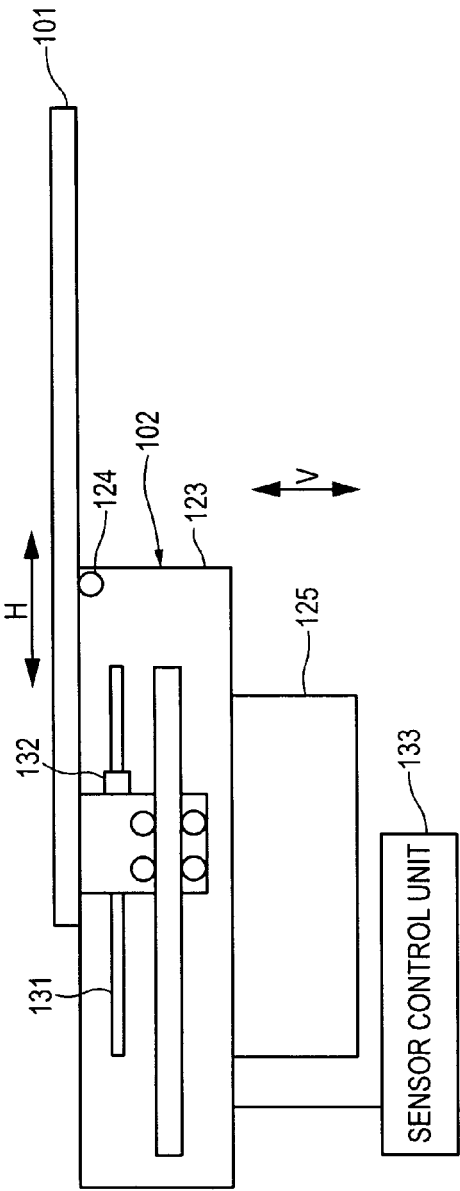

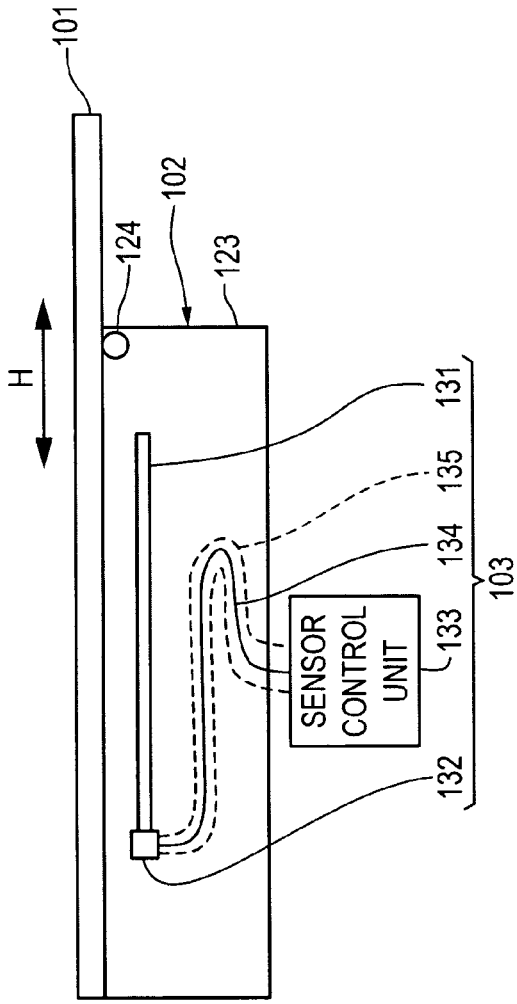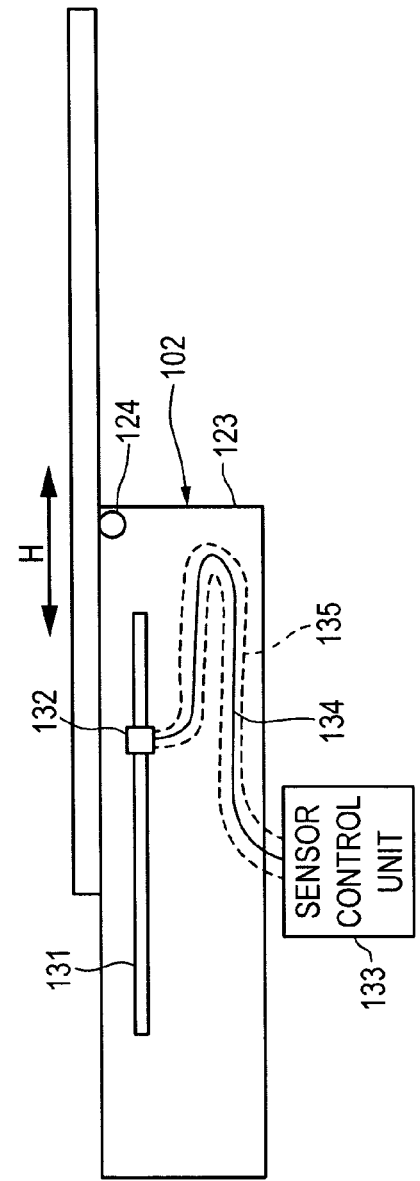

SUBJECT MOVING APPARATUS AND IMAGING APPARATUS

CROSS REFERENCE TO RELATED APPLICATIONS

This Application claims the benefit of Japanese Application No. 2004-248289 filed Aug. 27, 2004.

BACKGROUND OF THE INVENTION

The present invention relates to subject moving apparatus and an imaging apparatus, or more specifically, to an imaging apparatus that images a subject within an imaging space and subject moving apparatus that moves the subject into the imaging space in the imaging apparatus.

Imaging apparatus including an X-ray computed tomography (CT) system have subject moving apparatus that moves a subject into an imaging space. The imaging apparatus scans the subject, who is moved into the imaging space by the subject moving apparatus, so as to acquire raw data, and produces an image of the subject.

For example, in the case of the X-ray CT system, a subject is asked to lie down on a cradle included in the subject moving apparatus. Thereafter, the subject moving apparatus moves the cradle into the imaging space. Assuming that, for example, helical scan is performed, while the subject moving apparatus is sliding the cradle within the imaging space, an X-ray tube irradiates X-rays to the subject. An X-ray detector detects X-rays transmitted by the subject so that raw data will be acquired. Herein, the X-ray tube and X-ray detector rotate with the body-axis direction of the subject as an axis of rotation. X-rays are irradiated in directions of views around the subject, and raw data is acquired in each of the directions of views. At this time, the subject moving apparatus senses the position of the cradle and moves the cradle so that the cradle will be located at a position determined with conditions for scanning. The raw data items acquired in the respective directions of views are used to reconstruct a tomographic image of the subject under the conditions of a desired slicing position and slice thickness (refer to, for example, Patent Document 1).

[Patent Document 1] Japanese Unexamined Patent Application Publication No. 10-314162

In order to detect the position of a cradle on which a subject lies down, for example, a rotary housing is brought into contact with the cradle. A rotary encoder is used to acquire information on the number of rotations made by the rotary housing, whereby the position of the cradle is detected.

However, in order to enlarge a scanning range or shorten a scan time, the moving speed of the cradle is increased and the cradle is moved fast. Therefore, when the rotary encoder is used, a backlash or any other drawback takes place. Accordingly, an error in information on the position of the cradle may become significant. Eventually, since a subject cannot be scanned at a position determined with conditions for scanning, diagnostic efficiency deteriorates.

More particularly, in recent years, a scanning procedure for acquiring raw data while the cradle is not only moved at a certain speed but also accelerated or decelerated has been proposed. In this case, the above drawback becomes outstanding.

SUMMARY OF THE INVENTION

Therefore, an object of the present invention is to provide subject moving apparatus that highly precisely detects the position of a cradle on which a subject lies down, contributes to improvement in diagnostic efficiency, and makes quick movements, and an imaging apparatus.

In order to accomplish the above object, the present invention provides a subject moving apparatus that moves a subject into an imaging space in an imaging apparatus which images the subject in the imaging space. The subject moving apparatus comprises: a cradle on which the subject lies down; a cradle support that supports the cradle so that the cradle can be slid into the imaging space; and a cradle position sensing mechanism that senses a position into which the cradle is slid. The cradle position sensing mechanism includes a scale unit that has a scale, which is used to detect the position of the cradle, formed thereon and that is extended to cover a sliding range within which the cradle can be slid, and a sensor unit that is moved relatively to the scale unit in directions, in which the scale unit is extended, along with the slide of the cradle in order to detect the scale of the scale unit. Based on the reading on the scale detected by the sensor unit, the cradle position sensing mechanism calculates the position into which the cradle is slid.

The imaging apparatus in accordance with the present invention is an imaging apparatus that images a subject within an imaging space, and comprises: a cradle on which the subject lies down; a cradle support that supports the cradle so that the cradle will be slid into the imaging space; a cradle position sensing mechanism that senses a position into which the cradle is slid; a scanner that scans the subject, who is moved into the imaging space by sliding the cradle, so as to acquire raw data; and an image production unit that produces an image of the subject using the raw data acquired by the scanner. The cradle position sensing mechanism includes: a scale unit that has a scale, which is used to detect the position of the cradle, formed thereon and that is extended to cover a sliding range within which the cradle can be slid; and a sensor unit that is moved relatively to the scale unit in the directions, in which the scale unit is extended, along with the slide of the cradle and that detects the scale of the scale unit. Based on the reading on the scale detected by the sensor unit, the cradle position sensing mechanism calculates the position into which the cradle is slid.

According to the present invention, there is provided subject moving apparatus capable of highly precisely detecting the position of a cradle on which a subject lies down, contributing to improvement in diagnostic efficiency, and making quick movements, and an imaging apparatus.

Further objects and advantages of the present invention will be apparent from the following description of the preferred embodiments of the invention as illustrated in the accompanying drawings.

BRIEF DESCRIPTION OF THE DRAWINGS

FIGS. 4a and 4b illustrate side views showing subject moving apparatus included in the imaging apparatus in accordance with the embodiment of the present invention.

FIGS. 6a and 6b illustrate side views showing the connection of a sensor unit, which is included in a cradle position sensing mechanism included in the imaging apparatus in accordance with the embodiment of the present invention, to a sensor control unit included therein.

DETAILED DESCRIPTION OF THE INVENTION

An embodiment of the present invention will be described below.

Figure 1:
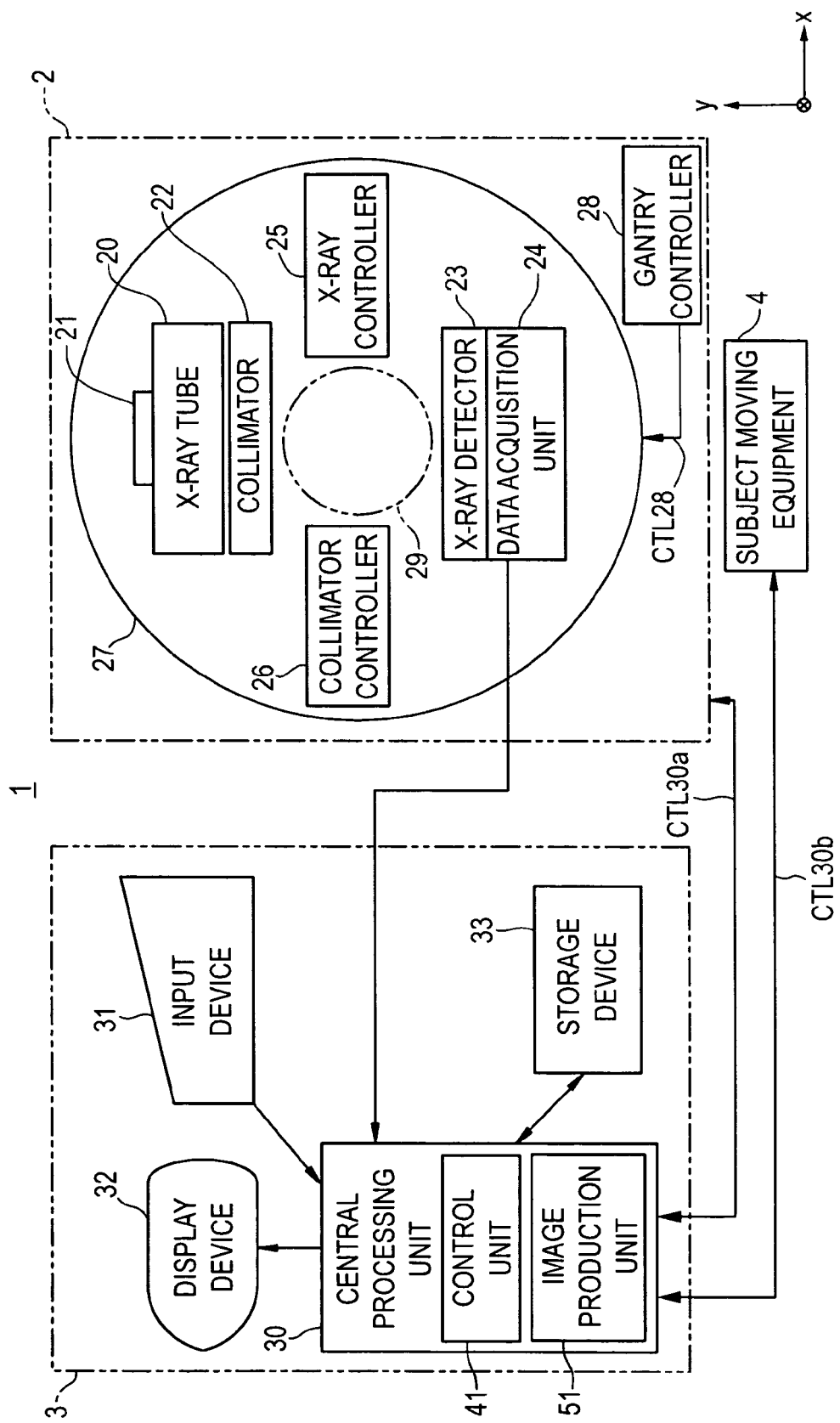
FIG. 1 is a block diagram showing the overall configuration of an imaging apparatus in accordance with an embodiment of the present invention.
Figure 2:
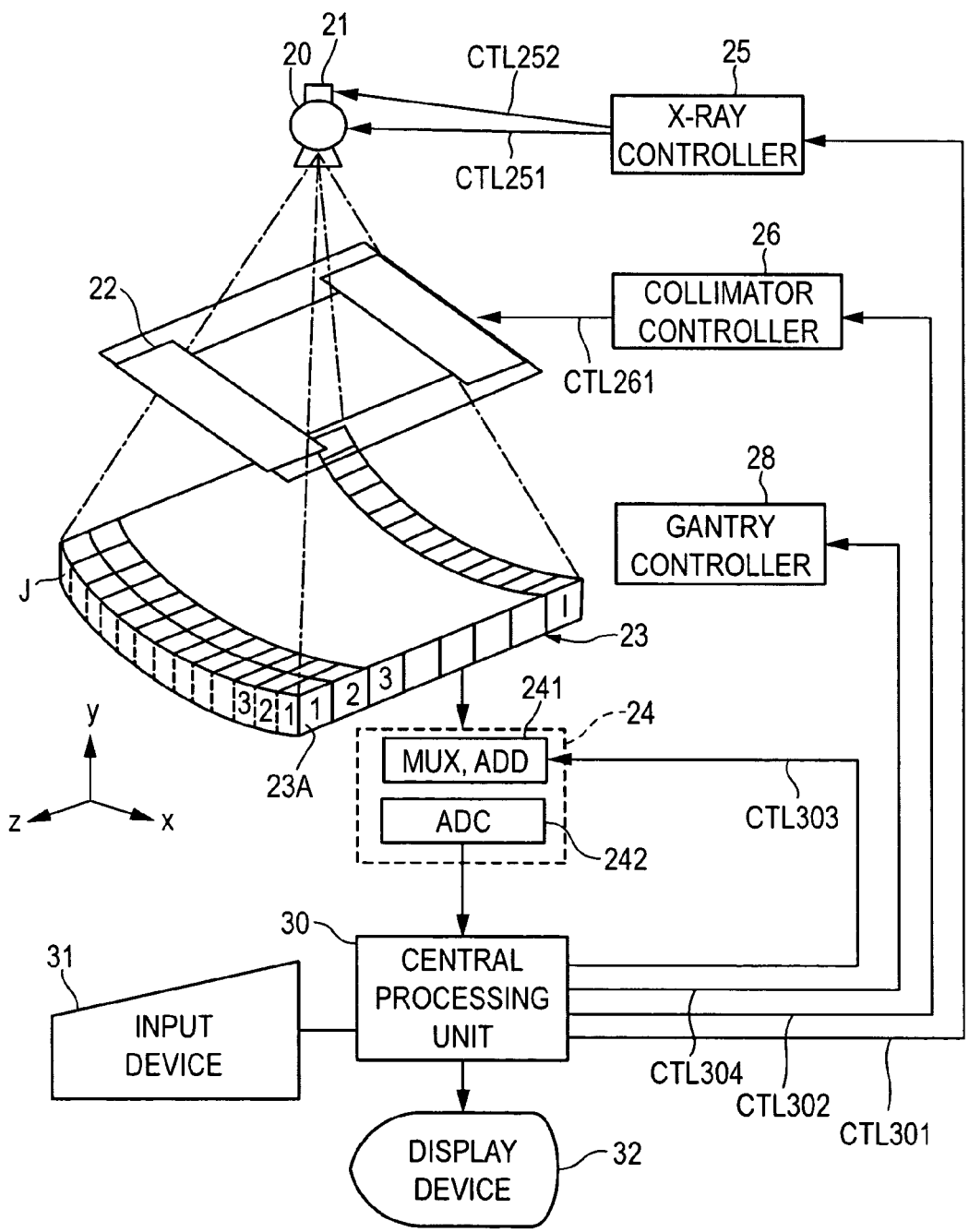
FIG. 2 shows the configuration of the major portion of the imaging apparatus in accordance with the embodiment of the present invention.

FIG. 1 is a block diagram showing the overall configuration of an X-ray CT system 1 that is an imaging apparatus in accordance with the embodiment of the present invention. FIG. 2 shows the configuration of the major portion of the X-ray CT system 1 in accordance with the embodiment of the present invention.

As shown in FIG. 1, the X-ray CT system 1 includes a scanner gantry 2, an operator console 3, and subject moving apparatus 4. The components will be orderly described below.

The scanner gantry 2 comprises an X-ray tube 20, an X-ray tube mover 21, a collimator 22, an X-ray detector 23, a data acquisition unit 24, an X-ray controller 25, a collimator controller 26, a rotary housing 27, and a gantry controller 28. The scanner gantry 2 scans a subject who is moved into an imaging space 29 by the subject moving apparatus 4, and acquires raw data. Herein, the X-ray tube 20 and X-ray detector 23 included in the scanner gantry 2 are opposed to each other with the imaging space 29, into which the subject is carried, between them.

The X-ray tube 20 is, for example, of a rotating anode type and irradiates X-rays. As shown in FIG. 2, the X-ray tube 20 irradiates X-rays of a predetermined intensity to a scan field in the subject via the collimator 22 according to a control signal CTL251 sent from the X-ray controller 25. Moreover, the X-ray tube 20 is rotated about the subject by the rotary housing 27 with a direction z of arrays, which corresponds to the body-axis direction of the subject, as an axis of rotation in order to irradiate X-rays in directions of views around the subject.

The X-ray tube mover 21 moves, as shown in FIG. 2, the central radiation port of the X-ray tube 20 in the direction z of arrays corresponding to the body-axis direction of the subject in the imaging space 29 of the scanner gantry 2 according to a control signal CTL252 sent from the X-ray controller 25.

The collimator 22 is, as shown in FIG. 2, interposed between the X-ray tube 20 and X-ray detector 23. The collimator 22 comprises, for example, two plates juxtaposed in a direction x of channels and two plates juxtaposed in the direction z of arrays. The collimator 22 moves the pairs of plates, which are juxtaposed in the respective directions, independently of each other according to a control signal CTL261 sent from the collimator controller 26, whereby X-rays irradiated from the X-ray tube 20 are blocked in the directions and recomposed into a conical beam. Thus, a range of X-irradiation is adjusted.

The X-ray detector 23 detects X-rays, which are irradiated from the X-ray tube 20 and transmitted by a subject, via the cradle 101 included in the subject moving apparatus 4, and acquires projection data of the subject as raw data to be used to construct an image. Herein, the X-ray detector 23 is rotated together with the X-ray tube 20 about the subject by the rotary housing 27 with the direction z of arrays as an axis of rotation. The X-ray detector 23 detects X-rays, which are transmitted by the subjects, in each of a plurality of directions of views around the subject, and produces projection data. The X-ray detector 23 has detector elements 23a two-dimensionally set in array in the direction x of channels corresponding to a direction, in which the X-ray tube 20 is rotated by the rotary housing 27 with the body-axis direction of the subject as an axis of rotation, and in the direction z of arrays substantially perpendicular to a plane defined with loci determined by rotation of the X-ray tube 20 made by the rotary housing 27. Moreover, the X-ray detector 23 has, as shown in FIG. 2, a plurality of X-ray detector modules 23A arranged in each of the direction x of channels and the direction z of arrays. The X-ray detector 23 has J X-ray detector modules 23A juxtaposed in the direction x of channels and I X-ray detector modules 23A juxtaposed in the direction z of arrays.

Figure 3:
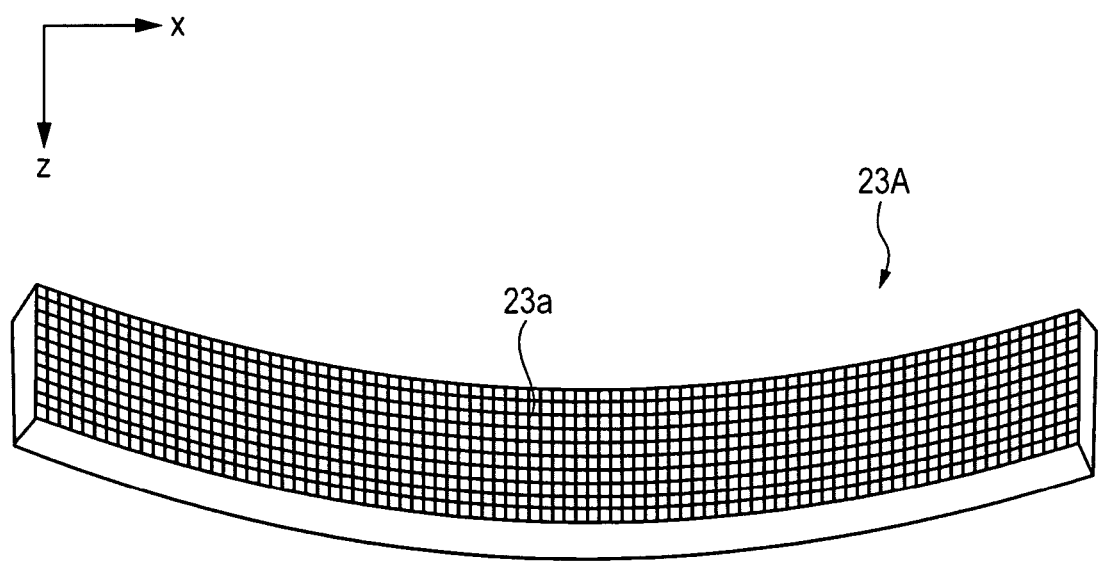
FIG. 3 shows the structure of an X-ray detector module included in an X-ray detector incorporated in the imaging apparatus in accordance with the embodiment of the present invention.

FIG. 3 shows the structure of the X-ray detector module 23A included in the X-ray detector 23. As shown in FIG. 3, the X-ray detector module 23A has the detector elements 23a, which detect X-rays, set in array in the direction x of channels and in the direction z of arrays. The plurality of two-dimensionally arranged detector elements 23a forms an X-ray incidence plane curved in a cylindrical concave manner. The X-ray detector module 23A has, for example, i detector elements 23a arranged in the direction x of channels and j detector elements 23a arranged in the direction z of arrays.

The detector element 23a is, for example, a solid detector and comprises a scintillator (not shown) that converts X-rays, which are transmitted by a subject, into light and a photodiode (not shown) that converts light, which is converted by the scintillator, into charge. The photodiodes included in the respective detector elements 23a are formed on the same substrate included in each X-ray detector module 23A. The detector element 23a is not limited to the detector element composed of the scintillator and photodiode. Alternatively, a semiconductor detector element utilizing cadmium telluride (CdTe) or an ion chamber type detector element 23a utilizing a xenon (Xe) gas will do.

The data acquisition unit 24 is included for acquiring data from X-rays detected by the X-ray detector 23. The data acquisition unit 24 acquires projection data of a subject from X-rays detected by the detector elements 23a included in the X-ray detector 23, and transmits the data to the operator console 3. As shown in FIG. 2, the data acquisition unit 24 comprises a selection/addition switching circuit (MUX, ADD) 241 and an analog-to-digital converter (ADC) 242. The selection/addition switching circuit 241 selects projection data, which is produced by the detector elements 23a included in the X-ray detector 23, according to a control signal CTL303 sent from a central processing unit 30, or summates projection data items, and transmits the result of selection or summation to the A/D converter 242. The A/D converter 242 converts projection data, which is selected by the selection/addition switching circuit 241 or calculated by summating any projection data items, from an analog signal to a digital signal, and transmits the digital signal to the central processing unit 30.

The X-ray controller 25 transmits, as shown in FIG. 2, a control signal CTL251 to the X-ray tube 20 according to a control signal CTL301 sent from the central processing unit 30, and thus controls X-irradiation. The X-ray controller 25 controls, for example, the tube current of the X-ray tube 20 or an irradiation time. Moreover, the X-ray controller 25 transmits a control signal CTL252 to the X-ray tube mover 221 according to the control signal CTL301 sent from the central processing unit 30, and thus controls the X-ray tube 20 so that the central radiation port of the X-ray tube 20 will be moved in the direction z of arrays.

The collimator controller 26 transmits, as shown in FIG. 2, a control signal CTL261 to the collimator 22 according to a control signal CTL302 sent from the central processing unit 30, and thus controls the collimator 22 so that the collimator 22 will recompose X-rays radiated from the X-ray tube 20.

The rotary housing 27 is, as shown in FIG. 1 and FIG. 2, rotated with the direction z of arrays, which corresponds to the body-axis direction of a subject, as an axis of rotation according to a control signal CTL28 sent from the gantry controller 28. The rotary housing 27 accommodates the X-ray tube 20, X-ray tube mover 21, collimator 22, X-ray detector 23, data acquisition unit 24, X-ray controller 25, and collimator controller 26. The rotary housing 27 rotates these components so as to change their positions relative to a subject who is moved into the imaging space 29. When the rotary housing 27 is rotated, X-rays are irradiated in a plurality of directions of views around the subject. The X-ray detector 23 detects X-rays transmitted by the subject in each of the directions of views. Moreover, the rotary housing 27 is tilted according to a control signal CTL28 sent from the gantry controller 28. The rotary housing 27 is tilted with an isocenter in the imaging space 29 as a fulcrum with respect to horizontal directions in which a subject is moved into or out of the imaging space 29 by the subject moving apparatus 4.

The gantry controller 28 transmits, as shown in FIG. 1 and FIG. 2, a control signal CTL28 to the rotary housing 27 according to a control signal CTL304 sent from the central processing unit 30 incorporated in the operator console 3, and thus causes the rotary housing 27 to rotate or tilt. The gantry controller 28 causes the rotary housing 27 to rotate, whereby X-rays are irradiated in a plurality of directions of views with the direction z of arrays, which corresponds to the body-axis direction of a subject, as an axis of rotation, and X-rays transmitted by the subject are detected. Moreover, the gantry controller 28 causes the rotary housing 27 to tilt with respect to the horizontal directions in which the subject is moved into or out of the imaging space 29 by the subject moving apparatus 4.

The operator console 3 comprises, as shown in FIG. 1, the central processing unit 30, an input device 31, a display device 32, and a storage device 33.

The central processing unit 30 is realized with, for example, a computer and includes, as shown in FIG. 1, a control unit 41 and an image production unit 51.

The control unit 41 controls components concerned so that X-rays will be irradiated from the X-ray tube 20 to a subject under the conditions for scanning the subject and X-rays transmitted by the subject will be detected by the X-ray detector 23. Specifically, the control unit 41 transmits a control signal CTL30a to the components concerned according to the conditions for scanning so that scan will be performed. For example, the control unit 41 transmits a control signal CTL30b to the subject moving apparatus 4 and thus causes the subject moving apparatus 4 to move the subject into or out of the imaging space 29. Moreover, the control unit 41 transmits a control signal CTL304 to the gantry controller 28 so as to cause the rotary housing 27 included in the scanner gantry 2 to rotate. The control unit 41 transmits a control signal CTL301 to the X-ray controller 25 so that X-rays will be radiated from the X-ray tube 20. The control unit 41 then transmits a control signal CTL302 to the collimator controller 26 so that the collimator 22 will be controlled to recompose X-rays. Moreover, the control unit 42 transmits a control signal CTL303 to the data acquisition unit 24 so that the data acquisition unit 24 will acquire projection data produced by the detector elements 23a included in the X-ray detector 23.

The image production unit 51 reconstructs a tomographic image of a subject according to raw data acquired by the scanner gantry 2. The image production unit 51 performs pre-processing such as sensitivity correction or beam hardening on projection data items acquired in the plurality of directions of views during helical scan, and then reconstructs a tomographic image of the subject according to a filtering back projection technique.

The input device 31 included in the operator console 3 is realized with, for example, an input device such as a keyboard or a mouse. The input device 31 transfers various pieces of information such as conditions for scanning or information on a subject to the central processing unit 30 responsively to operator's manipulations.

In response to a command issued from the central processing unit 30, a tomographic image of a subject reconstructed by the image production unit 51 is displayed on the display device 32.

The storage device 33 is realized with a memory. Various data items such as a tomographic image of a subject reconstructed by the image production unit 51 and programs are stored in the storage device 33. The data stored in the storage device 33 is accessed by the central processing unit 30 whenever it is needed.

The subject moving apparatus 4 is included for moving a subject into or out of the imaging space 29.

Figure 5:
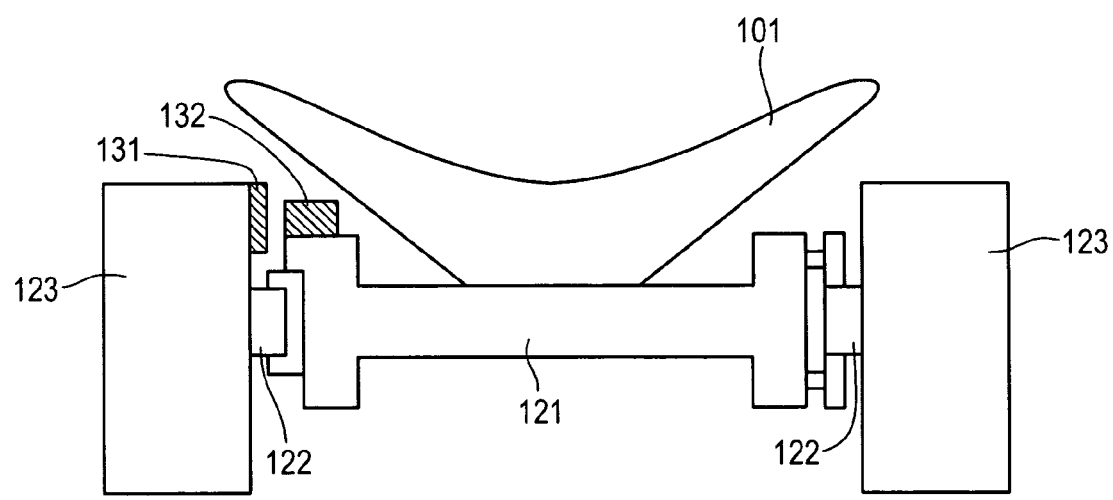
FIG. 5 is a front view showing the subject moving apparatus included in the imaging apparatus in accordance with the embodiment of the present invention.

FIG. 4 and FIG. 5 show the subject moving apparatus 4. FIG. 4 includes side views of the subject moving apparatus 4. FIG. 4(a) shows a state in which the cradle 101 included in the subject moving apparatus 4 is located outside the imaging space 29. FIG. 4(b) shows a state in which the cradle 101 is moving into the imaging space 29. Moreover, FIG. 5 is a front view of the subject moving apparatus 4 showing a carriage 121 shown in FIG. 4 and its surroundings.

As shown in FIG. 4, the subject moving apparatus 4 comprises the cradle 101, a cradle support 102, and a cradle position sensing mechanism 103.

The cradle 101 has a carrying surface on which a subject lies down and which bears the subject. The cradle 101 is, as shown in FIG. 4, supported by the cradle support 102, and movable in horizontal directions H substantially horizontal to the carrying surface and in vertical directions V substantially vertical to the carrying surface. The cradle 101 is moved between the inside and outside of the imaging space 29 in the scanner gantry 2. As shown in FIG. 4(b), the cradle 101 is fixed to the carriage 121 included in the cradle support 102, slid in the horizontal directions H together with the carriage 121, and moved to the inside of the imaging space 29 in the scanner gantry 2. Moreover, the X-ray detector 23 is located near the side of the cradle 101 opposite to the carrying surface side thereof on which a subject lies down.

The cradle support 102 supports the cradle 101 so that the cradle 101 can be slid into the imaging space 29. The cradle support 102 comprises, as shown in FIG. 4(a), the carriage 121, guide rails 122, guide rail bearings 123, a horizontal drive 124, and a vertical drive 125.

The carriage 121 serves as a cart that bears the cradle 101 and that slides the cradle 101 into the imaging space 29. As shown in FIG. 4 and FIG. 5, the carriage 121 is supported by the guide rails 122. The carriage 121 is fixed to an end of the cradle 101 away from the imaging space 29 in such a manner that the carriage 121 will not overlap an X-irradiation path between the X-ray tube 20 and X-ray detector 23. When the carriage 121 is slid in a direction in which the guide rails 122 are extended, the cradle 101 is slid into the imaging space 29. Moreover, a sensor unit 132 included in the cradle position sensing mechanism 103 is mounted on the carriage 121.

Along with the movement of the cradle 101, the sensor unit 132 mounted on the carriage 121 is slid to move.

The guide rails 122 are, as shown in FIG. 5, attached to the guide rail bearings 123, and extended in the directions in which the cradle 101 is slid. The guide rails 122 support the carriage 121 and allow the cradle 101 fixed to the carriage 121 to slide.

The guide rail bearings 123 are included for bearing the guide rails 122. The guide rail bearings 123 are, as shown in FIG. 5, for example, a pair of structures. The guide rails 122 are attached to the sides of the pair of structures that are opposed to each other, and borne thereby. The carriage 122 supported by the guide rails 123 are sandwiched between the pair of structures that are opposed to each other. Moreover, a scale unit 131 included in the cradle position sensing mechanism 103 is, as detailed later mounted on one of the guide rail bearings 123.

The horizontal drive 124 is included for causing the cradle 101 to slide in the horizontal directions H. The horizontal drive 124 includes, for example, a roller driving mechanism. Driving force exerted when an actuator drives a roller is conveyed to the cradle 101, whereby the cradle 101 is moved in the horizontal directions H.

The vertical drive 125 supports the cradle support 102 and moves the cradle 101, which is supported by the cradle support 102, in the vertical directions V. The vertical drive 125 includes, for example, a parallel link type driving mechanism. The vertical drive 125 uses, for example, an actuator (not shown) to drive parallel control arms, thus driving the cradle 101 in the vertical directions V.

The cradle position sensing mechanism 103 is included for sensing a position to which the cradle 101 is slid to move. The cradle position sensing mechanism 103 is a digital linear encoder and comprises, as shown in FIG. 4(a), the scale unit 131, the sensor unit 132, and a sensor control unit 133. Based on the reading on the scale detected by the sensor 131, the position to which the cradle 101 is slid to move is calculated.

FIG. 6 includes side views of the cradle position sensing mechanism 103 showing the connection between the sensor unit 132 and sensor control unit 133. FIG. 6(a) shows the state of the cradle position sensing mechanism 103 attained when the cradle 101 is located outside the imaging space 29. FIG. 6(b) shows the state of the cradle position sensing mechanism 103 attained when the cradle 101 is moving into the imaging space 29. For concise explanation, the carriage 121, guide rails 122, and vertical drive 125 shown in FIG. 4 are excluded from FIG. 6.

As shown in FIG. 6, the cradle position sensing mechanism 103 comprises, in addition to the scale unit 131, sensor unit 132, and sensor control unit 133, a cable 134 and a cable guide 135.

The scale unit 131 has a scale, which is used to detect the position of the cradle 101, formed thereon, and is extended to cover a sliding range within which the cradle 101 can be slid. As shown in FIG. 4 and FIG. 5, the scale unit 131 is mounted on one of the guide rail bearings 134 included in the cradle support 102 and extended in the direction in which the guide rails 122 are extended. The scale unit 131 is disposed in such a manner that it will not overlap an X-irradiation path between the X-ray tube 20 and X-ray detector 23. The scale unit 131 has the scale thereof realized with a magnetic scale. For example, the scale unit 131 employs a magnetic scale having a north pole and a south pole arranged with a certain pitch between them in the directions in which the cradle 101 is moved.

The sensor unit 132 includes a magnetic sensor that detects the magnetic scale included in the scale unit 131. The sensor unit 132 is mounted on the carriage 121 while being separated from the scale unit 131 with a certain space between them so that the sensor unit 132 will be in non-contact with the scale unit 131. Namely, the sensor unit 132 is disposed in such a manner that it will not overlap an X-irradiation path between the X-ray tube 20 and X-ray detector 23. When the cradle 101 is slid, the sensor unit 132 is moved relatively to the scale unit 131 in the direction in which the scale unit 131 is extended, and thus detects the scale included in the scale unit 131. The sensor control unit 133 is, as shown in FIG. 6, connected to the sensor unit 132 over the cable 134. The sensor unit 132 has its detecting action controlled by the sensor control unit 133.

The sensor control unit 133 is connected to the sensor unit 132 over the cable 134. The sensor control unit 133 transmits a control signal to the sensor unit 132 over the cable 134 so as to control the detecting action of the sensor unit 132. Moreover, the sensor control unit 133 receives scale information on the scale unit 131 detected by the sensor unit 132. Based on the reading on the scale detected by the sensor unit 132, the sensor control unit 133 calculates the position into which the cradle 101 is slid.

The cable 134 is formed to contain wires made of a conducting material and links the sensor unit 132 and sensor control unit 133. The cable 134 is sheathed in the cable guide 135 and has the movable range thereof restricted by the cable guide 135.

The cable guide 135 accommodates the cable 134 and restricts the movable range of the cable 134. The cable guide 135 is formed by concatenating a plurality of link members (not shown). The cable guide 135 has one end thereof fixed to the sensor control unit 133 and has the other end thereof fixed to the sensor unit 131. The plurality of link members constituting the cable guide 135 that is stretched straightly is curved with joints among the link members buckled. When the sensor unit 131 is moved along with the slide of the cradle 101, the cable guide 135 guides the cable 134 so that the cable 134 will move within a predetermined range and protects the cable 134.

The X-ray CT system 1 in accordance with the present invention corresponds to an imaging apparatus in accordance with the present invention. Moreover, the scanner gantry 2 included in the present embodiment corresponds to a scanner included in the present invention. The subject moving apparatus 4 included in the present embodiment corresponds to subject moving apparatus included in the present embodiment. The X-ray tube 20 included in the present embodiment corresponds to a radiation irradiator included in the present invention. The X-ray detector 23 included in the present embodiment corresponds to a radiation detector included in the present invention. The image production unit 51 included in the present embodiment corresponds to an image production unit included in the present invention. The cradle 101 included in the present embodiment corresponds to a cradle included in the present invention. The cradle support 102 included in the present embodiment corresponds to a cradle support included in the present invention. The cradle position sensing mechanism 103 included in the present embodiment corresponds to a cradle position sensing mechanism included in the present invention. The carriage 121 included in the present embodiment corresponds to a carriage included in the present invention. The guide rails 122 included in the present embodiment correspond to guide rails included in the present invention. The scale unit 131 included in the present embodiment corresponds to a scale unit included in the present invention. The sensor unit 132 included in the present embodiment corresponds to a sensor unit included in the present invention. The sensor control unit 133 included in the present embodiment corresponds to a sensor control unit included in the present invention. The cable 134 included in the present embodiment corresponds to a cable included in the present invention. The cable guide 135 included in the present embodiment corresponds to a cable guide included in the present invention.

A description will be made of actions to be performed in order to image a subject using the X-ray CT system 1 in accordance with the present embodiment.

For imaging a subject, the subject is asked to lie down on the cradle 101. Herein, the subject lies down on the carrying surface of the cradle 101 and is thus borne by the cradle 101.

Thereafter, conditions for scanning are determined. For determining the conditions for scanning, an operator uses the input device 31 to enter various parameters specified as the conditions for scanning. Parameters, for example, a scan technique such as a helical scan technique, the number of scans equivalent to the number of images to be produced, a tube current and a tube voltage of the X-ray tube 20, an X-irradiation time, a slicing position, and a slice thickness are determined as the conditions for scanning.

Thereafter, the subject is scanned. For scanning the subject, the control unit 41 transmits control signals CTL30a and CTL30b to the scanner gantry 2 and subject moving apparatus 4 respectively according to the determined conditions for scanning.

Consequently, the vertical drive 125 included in the subject moving apparatus 4 moves the cradle 101 in the vertical direction H so as to lift the cradle 101 up to the height of the imaging space 29 in the scanner gantry 2. Thereafter, the horizontal drive 124 slides the cradle 101 in the horizontal direction so as to move the cradle 101 into the imaging space 29 in the scanner gantry 2. The X-ray controller 25 transmits a control signal CTL252 to the X-ray tube 20, and the X-ray tube 20 irradiates X-rays. The collimator controller 26 transmits a control signal CTL302 to the collimator 22 so that the X-rays radiated from the X-ray tube 20 will be recomposed. Consequently, the gantry controller 28 transmits a control signal CTL28 to the scanner gantry 2 so that the rotary housing 27 of the scanner gantry 2 will be rotated. Moreover, the control unit 41 transmits a control signal CTL303 to the data acquisition unit 24 so that the data acquisition unit 24 will acquire as raw data projection data produced by the detector elements 23a included in the X-ray detector 23.

Specifically, when helical scan is performed, the cradle 101 on which the subject lies down is slid within the imaging space 29 in the direction in which the guide rails 122 are extended. The X-ray tube 20 irradiates X-rays to the subject in the plurality of directions of views, and the X-ray detector 23 detects X-rays transmitted by the subject via the cradle 101 in each of the directions of views. Consequently, raw data is acquired.

At this time, the cradle position sensing mechanism 103 included in the subject moving apparatus 4 senses a position into which the cradle 101 is slid during acquisition of raw data. As shown in FIG. 4, the sensor unit 132 moves relatively to the scale unit 131 in the directions, in which the scale unit 131 is extended, along with the slide of the cradle 101, and detects the scale included in the scale unit 131. Based on the reading on the scale detected by the sensor unit 132, the sensor control unit 133 calculates the position into which the cradle 101 is slid. When the sensor unit 131 moves along with the slide of the cradle 101, the cable guide 131 guides the cable 134 so that the cable 134 will move within a predetermined range and protects the cable 134.

Thereafter, the image production unit 51 reconstructs a tomographic image of the subject according to the raw data acquired in each of the directions of views under the conditions of a desired slicing position and a desired slice thickness. Herein, the image production unit 51 performs preprocessing such as sensitivity correction and beam hardening on projection data items detected in the plurality of directions of views. Thereafter, the image production unit 51 reconstructs a tomographic image of the subject according to a filtering back projection technique.

As mentioned above, according to the present embodiment, the sensor unit 132 included in the cradle position sensing mechanism 103 moves relatively to the scale unit 131 in the directions, in which the scale unit 131 is extended, along with the slide of the cradle 101. The sensor unit 132 then detects the scale included in the scale unit 131. Based on the reading on the scale detected by the sensor unit 132, the cradle position sensing mechanism 103 calculates a position into which the cradle is slid. Consequently, according to the present invention, occurrence of a drawback such as a backlash is rarer than it is when a rotary encoder is employed. Positional information on the cradle 101 can be detected with high precision. This leads to improvement in diagnostic efficiency and quick movements.

Moreover, according to the present embodiment, the sensor unit 132 included in the cradle position sensing mechanism 103 is mounted on the carriage 121 included in the cradle support 102. The scale unit 131 included in the cradle position sensing mechanism 103 is mounted on the cradle support 102 and extended in the direction in which the guide rails 122 included in the cradle support 102 are extended. As mentioned above, the X-ray detector 23 detects X-rays, which are transmitted by a subject, via the cradle 101 and produces raw data. Since the scale unit 131 and sensor unit 132 are not mounted on the cradle 101 but disposed not to overlap an X-irradiation path between the X-ray tube 20 and X-ray detector 23, X-rays transmitted by the subject will not be blocked by the scale unit 131 and sensor unit 132. Therefore, the present embodiment can highly precisely acquire raw data, contribute to improvement in diagnostic efficiency, and make quick movements.

According to the present embodiment, the cable 134 linking the sensor unit 132 and the sensor control unit 133 that controls the sensor unit 132 is sheathed in the cable guide 135. The cable guide 135 restricts the movable range of the cable 134. Therefore, according to the present embodiment, the cable guide 135 prevents the cable 134 from being entangled and broken due to the slide of the cradle 101. Consequently, the cradle 101 can be smoothly slid. The present embodiment can highly precisely detect positional information on the cradle 101, contribute to improvement in diagnostic efficiency, and make quick movements.

The present invention is not limited to the aforesaid embodiment but can be applied to various variants.

For example, although the cradle position sensing mechanism included in the aforesaid embodiment senses a position, into which the cradle is slid, using the scale unit having the scale thereof realized with a magnetic scale, and the sensor unit having the sensor thereof realized with a magnetic sensor that detects the magnetic scale, the present invention is not limited to this mode. For example, the cradle position sensing mechanism may sense the position, into which the cradle is slid, using a scale unit having a scale thereof realized with an optical scale, and a sensor unit having a sensor thereof realized with an optical sensor that detects the optical scale. For example, the cradle position sensing mechanism may comprise a scale unit that has as a scale a high-reflectance surface and a low-reflectance surface alternately juxtaposed in the directions in which the cradle is slid, and a sensor unit that includes a light-emitting element and a light-receiving element. Light reflected from the scale unit is sensed by the sensor unit, whereby a position into which the cradle is slid is sensed.

For example, the sensor included in the aforesaid embodiment is in non-contact with the scale unit. The present invention is not limited to this mode. Alternatively, the sensor may be in contact with the scale unit.

Moreover, for example, the aforesaid embodiment adopts X-rays as a radiation to be irradiated from a radiation irradiator. The present invention is not limited to this mode. Alternatively, for example, gamma rays or any other radiation may be adopted.

Many widely different embodiments of the invention may be configured without departing from the spirit and the scope of the present invention. It should be understood that the present invention is not limited to the specific embodiments described in the specification, except as defined in the appended claims.

The invention claimed is:

1. Subject moving apparatus included in an imaging apparatus, which images a subject within an imaging space, for moving the subject to the imaging space, comprising:
   a cradle on which the subject lies down;
   a cradle support that supports the cradle so that the cradle will be slid into the imaging space; and
   a cradle position sensing mechanism that senses a position into which the cradle is slid, wherein:
   the cradle position sensing mechanism comprises: a scale unit that has a scale, which is used to detect the position of the cradle, formed thereon and that is extended to cover a sliding range within which the cradle can be slid; and a sensor unit that is moved relatively to the scale unit in directions, in which the scale unit is extended, along with the slide of the cradle, and that detects the scale of the scale unit; and
   based on the reading on the scale detected by the sensor unit, the cradle position sensing mechanism calculates a position into which the cradle is slid.

2. The subject moving apparatus according to claim 1, wherein: the cradle support comprises a carriage that supports the cradle, and guide rails that extend in the directions, in which the cradle is slid, and support the carriage; and the sensor unit is mounted on the carriage, and the scale unit is mounted on the cradle support and extended in the directions in which the guide rails are extended.

3. The subject moving apparatus according to claim 2, wherein the cradle position sensing mechanism comprises: a sensor unit control unit that controls the sensor unit; a cable linking the sensor unit and the sensor unit control unit; and a cable guide that sheathes the cable and restricts the movable range of the cable.

4. The subject moving apparatus according to claim 1, wherein the scale unit has the scale thereof realized with a magnetic scale, and the sensor unit includes a magnetic sensor that detects the magnetic scale.

5. The subject moving apparatus according to claim 1, wherein the scale unit has the scale thereof realized with an optical scale, and the sensor unit includes an optical sensor that detects the optical scale.

6. The subject moving apparatus according to claim 1, wherein the sensor unit is separated from the scale unit with a certain space between them so that the sensor unit will be in non-contact with the scale unit.

7. The subject moving apparatus according to claim 1, wherein the sensor unit is disposed in contact with the scale unit.

8. An imaging apparatus for imaging a subject within an imaging space, comprising:
   a cradle on which the subject lies down;
   a cradle support that supports the cradle so that the cradle will be slid into the imaging space;
   a cradle position sensing mechanism that senses a position into which the cradle is slid;
   a scanner that scans the subject, who is moved into the imaging space by sliding the cradle, so as to acquire raw data; and
   an image production unit that produces an image of the subject according to the raw data acquired by the scanner, wherein:
   the cradle position sensing mechanism comprises: a scale unit that has a scale, which is used to detect the position of the cradle, formed thereon and that is extended to cover a sliding range within which the cradle can be slid; and a sensor unit that is moved relatively to the scale unit in directions, in which the scale unit is extended, along with the slide of the cradle, and that detects the scale of the scale unit; and
   based on the reading on the scale detected by the sensor unit, the cradle position sensing mechanism calculates a position into which the cradle is slid.

9. The imaging apparatus according to claim 8, wherein:
   the cradle support comprises a carriage that supports the cradle, and guide rails that are extended in the directions in which the cradle is slid and that support the carriage;
   the sensor unit is mounted on the carriage; and
   the scale unit is mounted on the cradle support and extended in the directions in which the guide rails are extended.

10. The imaging apparatus according to claim 9, wherein the cradle position sensing mechanism comprises: a sensor control unit that controls the sensor unit; a cable linking the sensor unit and the sensor control unit; and a cable guide that sheathes the cable and restricts the movable range of the cable.

11. The imaging apparatus according to claim 8, wherein the scale unit has the scale thereof realized with a magnetic scale, and the sensor unit includes a magnetic sensor that detects the magnetic scale.

12. The imaging apparatus according to claim 8, wherein the scale unit has the scale thereof realized with an optical scale, and the sensor unit includes an optical sensor that detects the optical scale.

13. The imaging apparatus according to claim 8, wherein the sensor unit is separated from the scale unit with a certain space between them so that the sensor unit will be in non-contact with the scale unit.

14. The imaging apparatus according to claim 8, wherein the sensor unit is disposed in contact with the scale unit.

15. The imaging apparatus according to claim 8, wherein the scanner includes a radiation irradiator that irradiates a radiation to the subject who is slid into the imaging space, and a radiation detector that detects the radiation, which is irradiated from the radiation irradiator and transmitted by the subject, so as to acquire the raw data.

16. The imaging apparatus according to claim 15, wherein the radiation irradiator irradiates X-rays as the radiation.

* * * * *